(12) United States Patent
Ford

(10) Patent No.: US 6,712,782 B2
(45) Date of Patent: Mar. 30, 2004

(54) BRACHYTHERAPY APPARATUS AND METHODS

(75) Inventor: John C. Ford, Marietta, GA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/853,459

(22) Filed: May 9, 2001

(65) Prior Publication Data

US 2002/0169410 A1 Nov. 14, 2002

(51) Int. Cl.[7] .................. A61M 37/00; A61M 29/00; A61M 36/00; A61M 3/00; A61M 5/00; A61N 1/30; A61N 5/00; A61K 9/22

(52) U.S. Cl. ............... 604/24; 604/21; 604/108; 604/891.1; 128/899; 600/1; 600/4; 600/5; 600/6; 600/7; 600/8

(58) Field of Search ............... 604/21, 24, 68, 604/891.1; 128/899; 600/1, 4, 5, 6, 7, 8

(56) References Cited

U.S. PATENT DOCUMENTS

| | | | | |
|---|---|---|---|---|
| 4,638,809 A | * | 1/1987 | Kuperus ............... | 600/4 |
| 5,460,592 A | * | 10/1995 | Langton et al. ......... | 600/7 |
| 5,681,260 A | * | 10/1997 | Ueda et al. ........... | 600/114 |
| 5,713,828 A | * | 2/1998 | Coniglione ........... | 600/7 |
| 5,845,646 A | * | 12/1998 | Lemelson ............ | 128/899 |
| 5,935,144 A | * | 8/1999 | Estabrook ............ | 606/169 |
| 5,976,119 A | * | 11/1999 | Spears et al. ........ | 604/508 |
| 6,168,577 B1 | * | 1/2001 | Niederjohn et al. ...... | 604/23 |
| 6,168,777 B1 | * | 1/2001 | Greff et al. ......... | 424/1.25 |
| 6,254,573 B1 | * | 7/2001 | Haim et al. .......... | 604/157 |
| 6,273,851 B1 | * | 8/2001 | Slater et al. ......... | 600/8 |
| 6,352,682 B2 | * | 3/2002 | Leavitt et al. ........ | 424/1.25 |
| 6,447,438 B1 | * | 9/2002 | Bernardi et al. ...... | 600/3 |

* cited by examiner

Primary Examiner—William C Doerrler
Assistant Examiner—Filip Zec
(74) Attorney, Agent, or Firm—Beyer Weaver & Thomas LLP

(57) ABSTRACT

A brachytherapy apparatus is composed of a tubular needle with forwardly protruding cutting edges at its tip, a holder supporting the needle and a driver for electromechanically causing the needle to undergo a continuous or oscillatory rotary motion around its axis and/or a reciprocating linear motion in the longitudinal direction such that its front opening at its tip can reliably reach a specified position inside a patient's tissue without being deflected or bowing when it encounters an obstruction such as a calcification or a small bone. Such motions may be provided by a piezoelectric hammer and a piezoelectric tamper. After the needle is thus correctly positioned, a brachytherapy device such as a radioactive seed or a reflector may be pushed through and out of the needle by means of a pusher as the needle is retracted to leave a track inside the tissue. A quickly hardening liquid may be thereafter injected through the needle to immobilize the deposited brachytherapy device. Another brachytherapy device may be deposited similarly after the needle is retracted by a specified distance. A plurality of brachytherapy devices may be preliminarily prepared as a unit having them linearly arranged inside a hardened liquid and mutually separated by specified distances such that they can be pushed together through the needle, or they may be injected together with a quickly hardening liquid.

29 Claims, 3 Drawing Sheets

BRACHYTHERAPY APPARATUS AND METHODS

FIELD OF THE INVENTION

This invention relates to apparatus for and methods in brachytherapy. More in particular, this invention relates to brachytherapy apparatus and methods for high precision implantation of antitumor agents and other devices used in brachytherapy in a patient's body.

BACKGROUND OF THE INVENTION

In the field of medicine, nuclear radiation may be used for diagnostic and therapeutic treatment of patients inflicted with cancer. Typically, more than half of these patients need radiation therapy either as a primary or as adjunct mode of treatment. Conventional medical radiation sources used in these treatments include large fixed-position machines such as linear accelerators, as well as small, transportable radiation generating probes which provide a boost therapy. In the latter treatment system, miniaturized probes capable of producing a high dose of radiation in a pre-defined geometry (seeds) are inserted into a treatment volume. This treatment is commonly referred to as brachytherapy because the radiation source is located close to or, in some cases, within the treatment volume.

The advantage of brachytherapy is that very high doses of ionizing radiation are delivered to a localized volume of tissue such that the radiation is supplied primarily to the treatment volume without significantly affecting tissues in adjacent volumes. This ability, when combined with a rapid reduction in the radiation dose as a function of distance, shields distant anatomies from spurious radiation. Hence, the technique has provided excellent results for localized control of various tumors.

In applications where tumors under treatment are in the patient's prostate gland, an applicator such as a perineal template is commonly employed with one or more probes that contain seeds or radiation sources. The template has an array of openings for accepting a plurality of sequential tandem brachytherapy probes or needles. During operation, the template is positioned near tumors to be treated and referenced to one or more scanned images before the seeds are inserted into the openings. For anatomical regions where there is no body cavity, the interstitial implantation of radioactive needles is preferred. The needles are typically long and hollow with small outer diameter and at least one sharp end to allow penetration through the tissue. Small gauge needles can deflect as they encounter obstructions such as calcification or changes in tissue impedance. A needle is easily bowed by a small bone.

During a brachytherapy operation, a physician needs to know the exact position of the seeds, as well as the radiation dosage distribution from these seeds. It is also desirable to quantify the radiation received by the surrounding organs. Images of the treatment area are obtained from modalities such as X-ray radiograph, computed tomography, magnetic resonance, ultrasound, or nuclear medicine scans of the patient during a treatment simulation procedure. The information obtained from the images is correlated with the position of the template or the needles for intracavity or interstitial treatment. The position of the seed inside the patient is determined relative to the needle and the template as a function of the needle length and orientation, minus a length of a remaining needle portion outside the template.

The radiation dose is computed by a dosimetry program by taking into consideration the intensity of the radioactive sources and their coordinates relative to the tumor. Needle bowing and deflection introduce errors in the coordinates of the radioactive seeds and results in miscalculation of the radiation dose. Implications of the error in the radiation dose calculation include underexposure of the tumor and exposure of normal tissue to harmful radiation.

In addition, bending of the needle may result in breaking of the needle in the tissue. This can cause tissue damage and may require surgery to remove the broken needle pieces.

SUMMARY OF THE INVENTION

It is therefore an aspect of some embodiments of this invention to provide an improved brachytherapy apparatus with which the bending and bowing of needle can be minimized or obviated such that the operator can correctly estimate the position of its tip from the portion of the needle outside the tissue.

It is another aspect of some embodiments of this invention to provide brachytherapy methods by which seeds and other kinds of brachytherapy devices can be deposited precisely where they are intended, mutually separated by specified distances and mutually in specified orientations.

A brachytherapy apparatus embodying this invention may be characterized as comprising a tubular needle, a holder supporting the needle and a driver for electromechanically causing the needle to move in its longitudinal direction inside a patient's tissue. In order to prevent deflection and bowing of the needle when it encounters an obstruction such as a calcification, the tip of the needle is serrated, or provided with two or more cutting edges which may be triangular, protruding forward and the driver serves to cause a rotary and/or longitudinal motion of the needle. The rotary motion may be continuous or periodic. A periodic rotary motion may be provided by means of a piezoelectric hammer with a handle striking an anvil attached to a main body securely holding the needle. A piezoelectric tamper, similarly structured, may be used to provide the needle with a reciprocating longitudinal motion. After it is ascertained that the tip of the needle has arrived at a specified target position inside the patient's tissue, a radioactive seed or whatever small object to be implanted in the patient tissue for brachytherapy is passed through the needle and pushed out thereof by a pusher, as the needle is slightly retracted to leave a track inside the tissue. Thereafter, a quickly hardening liquid may be injected through the needle to immobilize the deposited brachytherapy device. If desired, the needle may be retracted by a specified distance and another brachytherapy device may be similarly pushed through and out of the needle.

When a plurality of brachytherapy devices are deposited in a tissue, these devices may be preliminarily formed into a unit, fixed inside a hardened liquid so as to be linearly arranged and mutually separated by specified distances. Such a unit may be pushed through and out of a needle inserted into a patient's body. Alternatively, the needle may be retracted from the target position to leave a track, or a groove, inside the tissue and a plurality of brachytherapy devices may be injected through the needle into this track together with a quickly hardening liquid.

By using an apparatus and method embodying this invention, a needle can be reliably inserted into a patient's body without being deflected or bowing so as to have its front opening correctly positioned and brachytherapy devices can be deposited accurately where they are intended to be.

BRIEF DESCRIPTION OF THE DRAWINGS

The accompanying drawings, which are incorporated in and form a part of this specification, illustrate embodiments of the invention and, together with the description, serve to explain the principles of the invention. In the drawings.

Throughout herein, like or equivalent components are indicated by a same numeral and repetitious description may be omitted.

DETAILED DESCRIPTION OF THE INVENTION

The invention relates, in one aspect, to a needle to be inserted into a patient's body tissue for implanting a device. In addition to a radioactive seed, small objects of other kinds may be implanted, for example, for the purpose of brachytherapy such as a marker and a reflector. Throughout herein, small objects of all such kinds that may be implanted in a patient's body tissue for a brachytherapy purpose will be referred to as a brachytherapy device.

Figure 1:
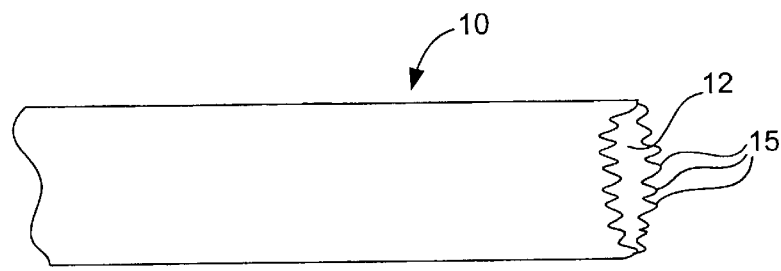
FIG. 1 is a schematic view of a needle serving as a part of a brachytherapy apparatus embodying this invention.

FIG. 1 shows an example of a needle 10, serving as a part of a brachytherapy apparatus embodying this invention, characterized not only as being hollow and cylindrical, extending in a longitudinal direction and having a front opening 12 at its tip, but also wherein its tip has sharp cutting edges 15 which protrude forward in the longitudinal direction for cutting tissue. Although FIG. 1 shows an embodiment with a large number of cutting edges 15 such that the tip may be described as forming a serrated edge with individual serration triangularly shaped, this is not intended to limit the scope of the invention. Preferred embodiments of the invention include needles with any number, two or larger, of forwardly protruding sharp edges. The edges may be, for example, equally spaced azimuthally around the central axis of the cylindrical needle extending in the longitudinal direction.

Figure 2:
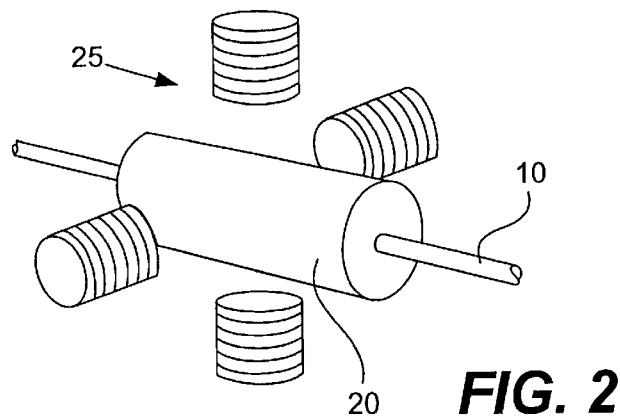
FIG. 2 is a schematic view of a needle of a brachytherapy apparatus of this invention with a means for providing it with a rotary motion.

A brachytherapy apparatus according to this invention is further characterized as having a holder supporting the needle and a driver (not shown in FIG. 1) for electromechanically causing the needle to advance in the longitudinal direction in the tissue even when the tip of the needle 10 has encountered obstructions such as calcification or changes in tissue impedance which may tend to cause deflection and/or bowing of the needle 10 as it is pushed further forward. The driver includes means for causing the needle 10 to rotate around the needle axis either continuously as in conventional drilling or reciprocatingly (or oscillatingly) with a specified or unspecified angular amplitude, as well as means for pushing the needle 10 in the longitudinal direction. For imparting a rotary motion, a rotor armature 20 may be affixed to the needle 10 with electromagnetic coils 25 provided, as schematically shown in FIG. 2 to form a motor.

Figure 3:
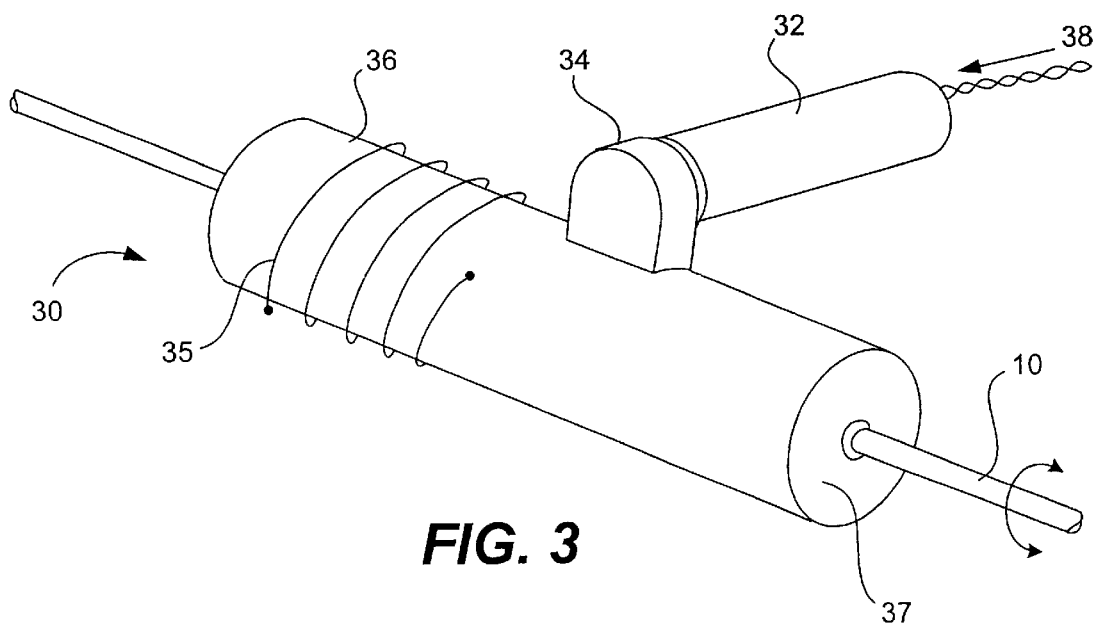
FIG. 3 is a schematic view of a piezoelectric hammer.

An electric motor may be used for both the continuous and the oscillatory mode of the rotation of the needle 10. In order to assure high precision needle implantation and to minimize damage to the tissue, the driver according to this invention may comprise a so-called piezoelectric hammer capable of producing very small angular displacements. FIG. 3 shows schematically such a piezoelectric hammer 30, including a handle 32, an anvil 34 and an elongated body 36. The elongated body 36 is oriented transversely to the axis of the handle 32 and has a cylindrical opening 37 extending longitudinally to accommodate the needle 10, serving as a holder therefor. A torsion spring 35 for providing a counter torque surrounds the body 36. As the piezoelectric hammer 30 is activated by a signal 38, the handle 32 strikes the anvil 34 in the direction transverse to the longitudinal direction of the needle 10, thereby causing both the elongated body 36 of the piezoelectric hammer 30 and the needle 10 itself to rotate against the biasing counter torque furnished by the torsion spring 35. The counter torque by the torsion spring 35 causes the needle 10 to return to its original angular orientation around the needle axis until the next signal 38 is received to activate the piezoelectric hammer 30. An oscillatory angular motion with angular amplitude on the order of 1 degree can thus be achieved.

Although not separately illustrated, the needle 10 may be affixed to the elongated body 36 or may be slidable longitudinally through the cylindrical opening 37 although the needle 10 and the elongated body 36 are adapted to rotate together around the needle axis. This may be accomplished, for example, by making piezoelectric elements annular such that the needle can pass therethrough.

Figure 4:
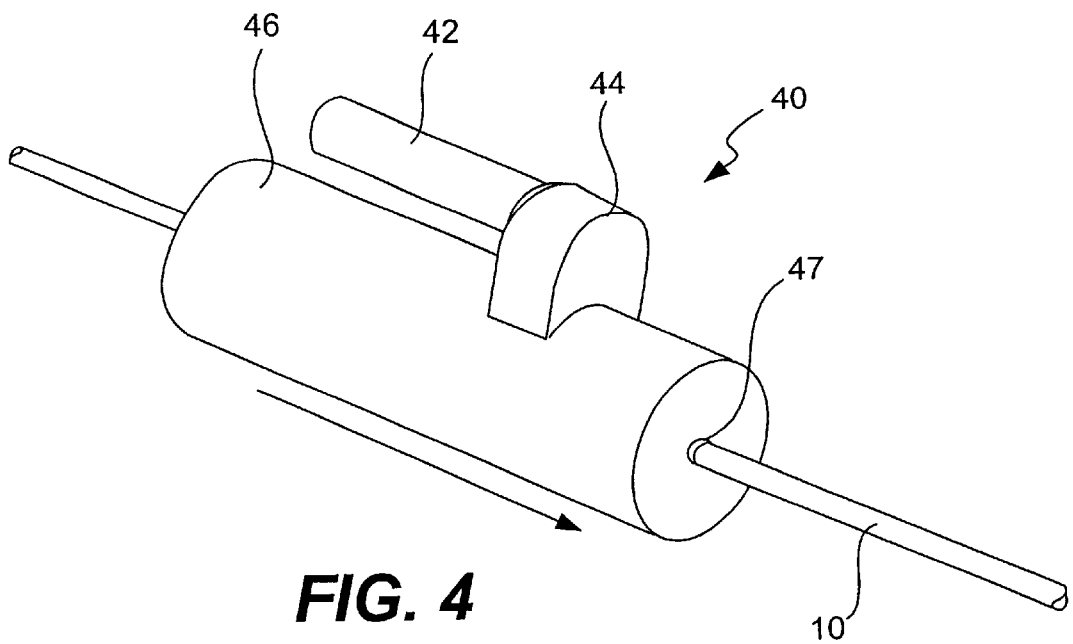
FIG. 4 is a schematic view of a piezoelectric tamper.

The driver may further include means for causing the needle 10 to undergo an oscillatory motion in the longitudinal direction, or to make small longitudinal displacements into the tissue by tamping. Such tamping may be effected by means of a piezoelectric tamper 40 such as shown in FIG. 4, having a handle 42, an anvil 44 and a body 46 which is elongated parallel to the handle 42 and has a cylindrical opening 47 extending longitudinally to accommodate the needle 10, serving as a holder therefor. As the piezoelectric tamper 40 is activated by a signal (not shown), the handle 42 strikes the anvil 44 which is attached to the body 46, thereby causing the needle 10 to be pushed forward in its longitudinal direction. Small longitudinal displacements allow for a very energetic thrust of the needle 10, resulting, for example, in fracture of calcification and reduction of needle friction. It is also important to have very small longitudinal displacements in order to assure accuracy in the placement of the implants and to avoid tissue damage.

Figure 5:
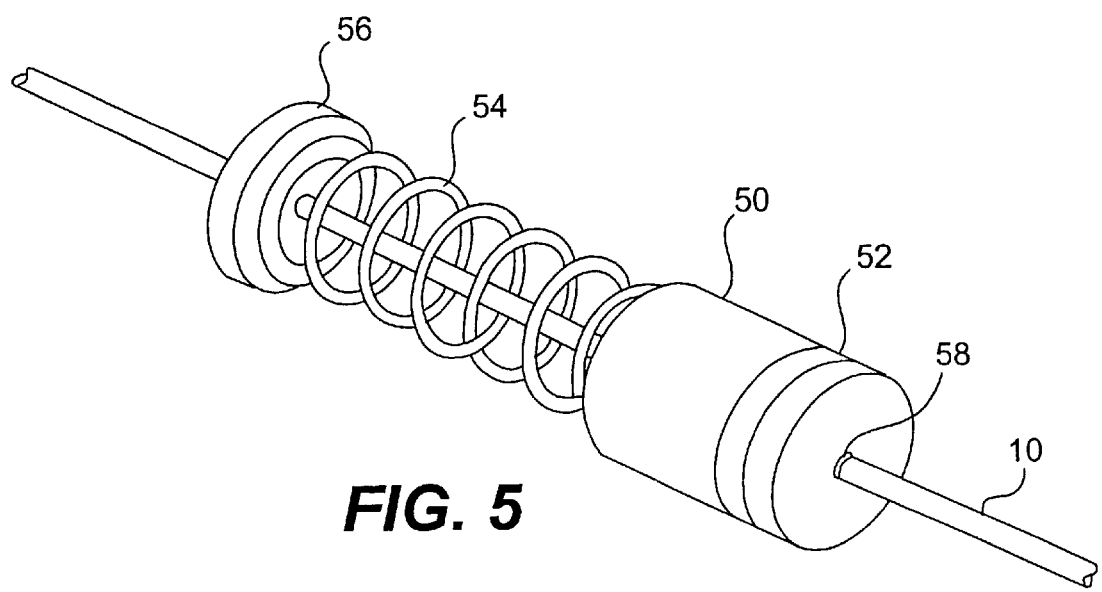
FIG. 5 is a schematic view of another brachytherapy apparatus combining a piezoelectric hammer for a rotary motion and a piezoelectric tamper for a longitudinal motion.

Although piezoelectric devices for causing rotary motion and longitudinal motion of the needle 10 have been separately disclosed above, many modifications and variations are possible within the scope of the invention, and, as one such variation they may also be combined in a single driving unit. FIG. 5 shows such a combined actuator, having a piezoelectric hammer 50 imparting a rotary motion and a piezoelectric tamper 52 imparting a longitudinal displacement, both formed in an annular shape with a needle 10 slidably passing through a cylindrical opening 58 therethrough. A torsion spring 54 is supported by a back stop 56 for limiting the range of the longitudinal motion of the actuator. Such a combined actuator may be used either separately or in combination and the excitation can be continuous, halted when a brachytherapy device is deposited, or modulated, say, depending upon the impedance encountered by the needle 10.

It will be appreciated that the present invention comprises providing some type of motion (in addition to the insertion into the tissue) that will assist the needle in penetrating a relatively hard portion of the tissue. As a further example, an orbital motion may be provided, for example, by biasing the needle against an eccentric cam. As yet another example, vibrational movement may be imparted to the needle. The vibrational movement may, if desired, be produced by a transducer within the holder. Alternatively, it may be produced remotely from the needle and transmitted to it via any portion of the apparatus directly or indirectly in contact with the needle. It will be understood that the needle undergoes a certain type of motion within the meaning of the present invention when such motion comprises at least a component of its overall motion. For example, an orbital motion would fall within the meaning of both reciprocating longitudinal motion and tamping motion. As another example, vibrational motion, which may be regular or random, would generally have a component of and therefore fall within the meaning of one or more of the other types of motions described herein. Accordingly, the terms are not meant to be mutually exclusive.

In another aspect, the invention relates to methods of using such an apparatus as described above for implanting a plurality of brachytherapy devices separated by specified distances.

Figure 6:
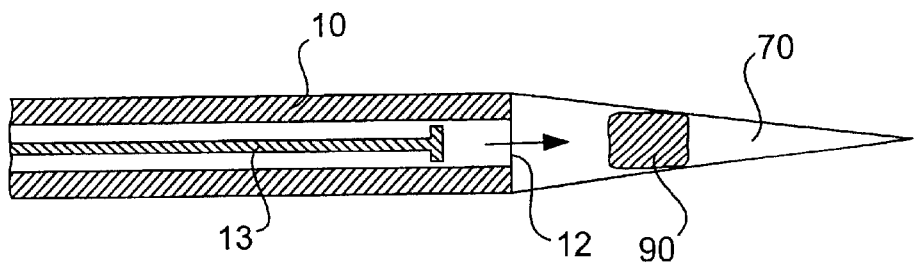
FIG. 6 is a schematic sectional view of a brachytherapy device being deposited according to a method of this invention.
Figure 7:
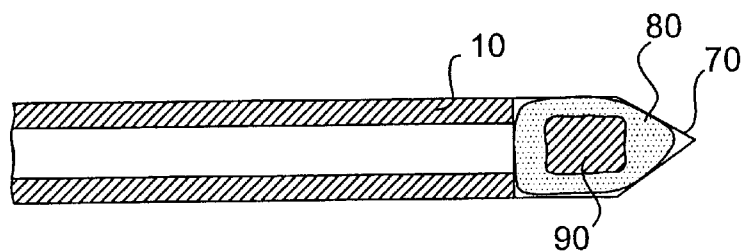
FIG. 7 is a schematic sectional view of a brachytherapy device being deposited according to another method of this invention.

After a needle 10 as described above is inserted into a patient's body and advanced against calcifications and other possible causes for needle deflection and bowing, for example, by using an actuator of a kind described above, such that it has been ascertained that its tip is now at a target position as schematically shown in FIG. 6, a brachytherapy device 90 of a selected kind is pushed through the needle 10 by means of a pusher 13 of a known kind and out of the front opening 12 at its tip as the needle 10 is slightly retracted so as to leave a track 70, or a groove which is long enough inside the tissue for accepting the device 90 which has been pushed out of the needle 10. If it is found to be desirable, a quickly hardening liquid 80 may be thereafter injected through the needle, say, from a syringe (not shown) to envelope the device 90, as shown in FIG. 7. Throughout herein, the expression "quickly hardening" is intended to be interpreted as meaning that the liquid becomes hard enough and quickly enough to prevent the deposited brachytherapy device 90 from becoming significantly displaced inside the tissue.

If it is desired that another brachytherapy device be deposited at another position separated from the first target position by a specified distance, the needle 10 is retracted by this specified distance and the process described above is repeated.

Figure 8:
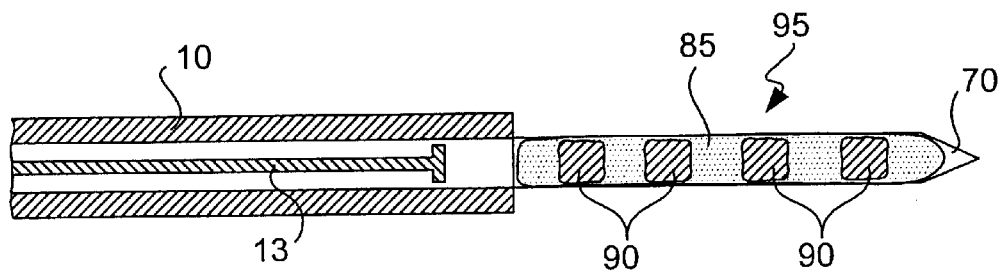
FIG. 8 is a schematic sectional view of a plurality of brachytherapy devices formed as a unit being deposited according to still another method of this invention.

Another method of depositing a plurality of brachytherapy devices in a linear arrangement and mutually separated by specified distances is to prepare a brachytherapy device unit 95 as shown in FIG. 8 having a desired plural number of brachytherapy devices 90 contacting and contained inside a hardened liquid material body 85, arranged linearly and sequentially separated by specified distances. The unit 95 thus formed is pushed through the needle 20 which is inserted into a patient's body with its tip at a specified position. After the needle 20 is retracted to leave a track 70, as described above with reference to FIGS. 6 and 7, or as the needle 20 is being retracted, the unit 95 is pushed out of the needle by a pusher 13 and deposited in the track 79 inside the tissue. This method is advantageous because not only the distance between each of the mutually adjacent pairs of linearly arranged brachytherapy devices 90 can be accurately controlled but also their orientation can be controlled when the unit 65 is formed. Since the field distribution of radiation from each seed is known, it is sometimes very important to arrange individual seeds in a certain orientational relationship in order to obtain a desired overall effect from a plurality of seeds.

Figure 9:
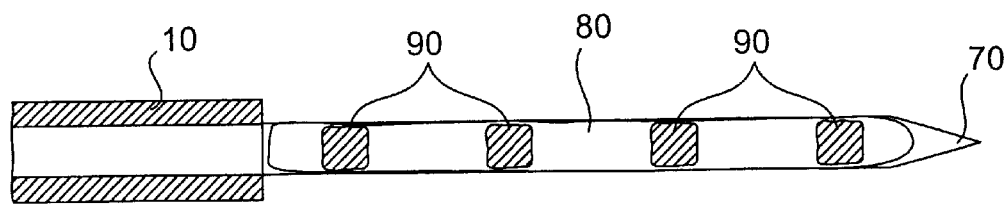
FIG. 9 is a schematic sectional view of brachytherapy devices being deposited with the injection of a quickly hardening liquid according to still another method of this invention.

Still another method of depositing a plurality of brachytherapy devices sequentially in a patient's tissue is, as schematically shown in FIG. 9, to retract a needle 10 which has once been inserted to a target position inside a patient's body to leave a track 70 and then push the plurality of brachytherapy devices 90 through and out of the needle 10 sequentially by the force of a quickly hardening liquid 80 which is injected out of the needle 10 simultaneously with the brachytherapy devices 90. The brachytherapy devices 90 thus pushed out of the needle 10 are immediately enveloped inside the track 70 by the quickly hardening liquid 80 and become affixed.

Although the invention was described above with reference to only a few examples, these examples are not intended to limit the scope of the invention. Many modifications and variations are possible within the scope of the invention. Aspects described in conjunction with one embodiment may be used in other embodiments. For example, a plurality of brachytherapy devices may be tied together to form a unit adapted to be pushed through the needle by means of a pusher. Although the invention has been described in conjunction with inserting a needle into a patient and injecting brachytherapy devices into the patient, the invention is applicable to other applications for inserting a needle, tubular member, probe or like structure into any mass, and, if desired, injecting an object into the mass through such insertion means. In summary, the disclosure is intended to be interpreted broadly and all such modifications and variations that may be apparent to a person skilled in the art are intended to be within the scope of the invention.

What is claimed is:

1. An apparatus comprising:
    a tubular brachytherapy needle extending in a longitudinal direction and having a tip with a front opening to be inserted into tissue;
    a holder supporting said needle; and
    a driver for electromechanically assisting said needle to move in said longitudinal direction in said tissue.

2. An apparatus comprising:
    a tubular needle extending in a longitudinal direction and having a tip with a front opening to be inserted into tissue;
    a holder supporting said needle; and
    a driver for electromechanically assisting said needle to move in said longitudinal direction in said tissue and causing said needle to undergo a rotary motion around said longitudinal direction.

3. The apparatus of claim 2 wherein said driver causes said needle to undergo a reciprocating oscillatory rotary motion around said longitudinal direction.

4. The apparatus of claim 1 wherein said driver causes said needle to undergo a reciprocating linear motion in said longitudinal direction.

5. The apparatus of claim 2 wherein said driver include a rotor armature affixed to said tubular needle and electromagnetic coils for causing said rotor armature to rotate.

6. The apparatus of claim 1 wherein said driver include an anvil attached to said needle and a piezoelectric hammer adapted to tap on said anvil.

7. The apparatus of claim 2 wherein said driver include an anvil attached to said needle and a piezoelectric hammer adapted to tap on said anvil.

8. The apparatus of claim 3 wherein said driver include an anvil attached to said needle and a piezoelectric hammer adapted to tap on said anvil.

9. The apparatus of claim 1 wherein said tip of said needle has a plurality of cutting edges protruding in said longitudinal direction, said cutting edges being at a constant angular pitch around said longitudinal direction.

10. An apparatus comprising:
   insertion means extending in a longitudinal direction and having an end to be inserted into tissue;
   holding means to support said insertion means; and
   driving means for electromechanically assisting said insertion means to move in said longitudinal direction in said tissue and causing said insertion means to undergo a rotary motion around said longitudinal direction.

11. The apparatus of claim 10 wherein said driving means causes said insertion means to undergo an oscillatory rotary motion around said longitudinal direction.

12. The apparatus of claim 10 wherein said driving means causes said insertion means to undergo an oscillatory linear motion in said longitudinal direction.

13. The apparatus of claim 10 wherein said driving means includes a rotor armature affixed to said insertion means and electromagnetic coils for causing said rotor armature to rotate.

14. The apparatus of claim 10 wherein said driving means includes an anvil attached to said insertion means and a piezoelectric hammer adapted to tap on said anvil.

15. An apparatus comprising:
   a brachytherapy needle extending in a longitudinal direction and having a tip with a front opening to be inserted into tissue;
   a holder supporting said needle; and
   a driver causing said needle to move in one or more of a rotating, longitudinal reciprocating, tamping, vibrational or orbital motion during at least a portion of time during which said needle is inserted into the tissue.

16. A method comprising the steps of:
   providing a tubular brachytherapy needle extending in a longitudinal direction and having a tip with a front opening;
   inserting said needle from said tip into tissue;
   electromechanically causing said needle to move in said longitudinal direction in said tissue; and
   causing a brachytherapy device to pass through said brachytherapy needle and to be deposited through said tip at a specified position inside said tissue.

17. The method of claim 16 wherein said brachytherapy needle is caused to undergo a rotary motion around said longitudinal direction.

18. The method of claim 17 wherein said brachytherapy needle is caused to undergo a reciprocating oscillatory rotary motion around said longitudinal direction.

19. The method of claim 16 wherein said brachytherapy needle is caused to undergo a reciprocating linear motion in said longitudinal direction.

20. The method of claim 17 wherein a rotor armature is affixed to said tubular brachytherapy needle and electromagnetic coils are provided for causing said rotor armature to rotate.

21. The method of claim 16 wherein an anvil is attached to said brachytherapy needle and a piezoelectric hammer is provided to tap on said anvil.

22. The method of claim 17 wherein an anvil is attached to said brachytherapy needle and a piezoelectric hammer is provided to tap on said anvil.

23. The method of claim 18 wherein an anvil is attached to said brachytherapy needle and a piezoelectric hammer is provided to tap on said anvil.

24. The method of claim 16 wherein said tip of said brachytherapy needle has a plurality of cutting edges protruding in said longitudinal direction, said cutting edges being at a constant angular pitch around said longitudinal direction.

25. A method comprising the steps of:
   providing a tubular brachytherapy needle extending in a longitudinal direction and having a tip with a front opening;
   inserting said brachytherapy needle from said tip into tissue until said front opening is at a specified position;
   pushing a brachytherapy device through said brachytherapy needle and depositing said brachytherapy device at said specified position;
   thereafter moving said brachytherapy needle inside said issue by a specified distance to bring said tip to another specified position; and
   thereafter pushing another brachytherapy device through said brachytherapy needle and depositing said another brachytherapy device at said another specified position.

26. A method comprising the steps of:
   providing a tubular needle extending in a longitudinal direction and having a tip with a front opening;
   inserting said needle from said tip into tissue until said front opening is at a specified position;
   pushing a brachytherapy device through said needle and depositing said brachytherapy device at said specified position; and
   thereafter injecting a quickly hardening liquid through said needle to cause said deposited brachytherapy device to remain at said specified position.

27. A method comprising the steps of:
   providing a tubular needle extending in a longitudinal direction and having a tip with a front opening;
   inserting said needle from said tip into tissue until said front opening is at a specified position;
   providing a brachytherapy unit containing a plurality of brachytherapy devices arranged sequentially inside a material so as to be mutually separated by specified distances; and
   pushing said unit through said needle in said longitudinal direction and depositing said brachytherapy device at said specified position.

28. The method of claim 27 wherein said plurality of brachytherapy devices are arranged within said material in specified mutual orientations.

29. A method comprising the steps of:
   providing a tubular needle extending in a longitudinal direction and having a tip with a front opening;
   inserting said needle from said tip in said longitudinal direction into tissue and withdrawing said needle so as to leave a longitudinal groove inside said tissue; and
   pushing one or more brachytherapy devices sequentially through said needle and out of said needle into said groove by injecting a quickly hardening liquid through said needle, thereby causing said liquid to harden inside said groove around said deposited brachytherapy devices.

* * * * *